(12) United States Patent
Jeffrey et al.

(10) Patent No.: US 9,788,938 B2
(45) Date of Patent: Oct. 17, 2017

(54) INTRAOCULAR MANIPULATOR AND RELATED METHODS

(71) Applicant: The Regents of the University of Colorado, a Body Corporate, Denver, CO (US)

(72) Inventors: Olson Jeffrey, Cherry Hills Village, CO (US); Douglas Leroy MacKenzie, Englewood, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 424 days.

(21) Appl. No.: 14/347,732

(22) PCT Filed: Oct. 4, 2012

(86) PCT No.: PCT/US2012/058612
§ 371 (c)(1),
(2) Date: Mar. 27, 2014

(87) PCT Pub. No.: WO2013/052578
PCT Pub. Date: Apr. 11, 2013

(65) Prior Publication Data
US 2014/0236163 A1   Aug. 21, 2014

Related U.S. Application Data

(60) Provisional application No. 61/543,617, filed on Oct. 5, 2011.

(51) Int. Cl.
*A61F 9/007* (2006.01)
*A61F 2/16* (2006.01)

(52) U.S. Cl.
CPC ............ *A61F 2/1662* (2013.01); *A61F 9/007* (2013.01); *A61F 9/00709* (2013.01); *A61F 2/1664* (2013.01)

(58) Field of Classification Search
CPC . A61B 1/00094; A61B 17/2031; A61B 17/28; A61B 2017/306; A61B 2017/308;
(Continued)

(56) References Cited

U.S. PATENT DOCUMENTS 2,164,926 A * 7/1939 Kleine ............ A61M 25/09025
604/170.02
2,379,629 A * 7/1945 Eweson ................ A61F 9/0061
294/1.2
(Continued)

OTHER PUBLICATIONS

International Search Report and Written Opinion in PCT/US2012/058612 dated Mar. 25, 2013.
(Continued)

*Primary Examiner* — Ryan J Severson
(74) *Attorney, Agent, or Firm* — Snell & Wilmer L.L.P.

(57) ABSTRACT

In accordance with various embodiments, an intraocular manipulator is disclosed which uses negative pressure to grasp and/or manipulate an intraocular object, for example, an IOL, a crystalline lens, or an intraocular foreign body. The device comprises a tip, a stem, and a suction source. The device may be a handheld device with the negative pressure controlled by a foot pedal. Similarly, the device may be used in conjunction with other intraocular devices.

15 Claims, 6 Drawing Sheets

(58) Field of Classification Search
CPC ..... A61B 2018/00291; A61B 5/150145; A61F 2/1662; A61F 2/1664; A61F 2/1675; A61F 2/1691; A61F 9/007; A61F 9/00709; A61F 9/00736; A61F 9/013
See application file for complete search history.

(56) References Cited

U.S. PATENT DOCUMENTS

| | | | | |
|---|---|---|---|---|
| 2,555,076 | A * | 5/1951 | Crossley | A61B 17/50 606/107 |
| 2,590,527 | A * | 3/1952 | Fluck | A61H 9/005 15/397 |
| 3,074,407 | A * | 1/1963 | Moon | A61F 9/013 606/166 |
| 3,177,874 | A * | 4/1965 | Spriggs | A61F 9/0061 206/5 |
| 3,424,486 | A * | 1/1969 | Clifton | A61F 9/0061 294/1.2 |
| 3,592,193 | A * | 7/1971 | Higgins | A61M 25/065 604/161 |
| 3,879,076 | A * | 4/1975 | Barnett | A61F 9/0061 294/1.2 |
| 3,912,317 | A * | 10/1975 | Ohnaka | B25J 9/144 294/186 |
| 4,047,532 | A | 9/1977 | Phillips et al. | |
| 4,049,000 | A * | 9/1977 | Williams | A61M 1/0047 433/95 |
| 4,079,976 | A | 3/1978 | Rainin | |
| 4,123,098 | A * | 10/1978 | Shoup | A61F 9/0061 294/1.2 |
| 4,286,815 | A | 9/1981 | Clark | |
| 4,688,570 | A * | 8/1987 | Kramer | A61F 9/013 606/166 |
| 5,009,660 | A * | 4/1991 | Clapham | A61F 9/009 604/294 |
| 5,019,086 | A * | 5/1991 | Neward | A61B 17/442 606/123 |
| 5,290,082 | A * | 3/1994 | Palmer | B25B 11/007 29/743 |
| 5,437,651 | A * | 8/1995 | Todd | A61M 1/0088 15/420 |
| 5,649,727 | A * | 7/1997 | St. Louis | A61F 9/0061 294/1.2 |
| 5,984,864 | A * | 11/1999 | Fox | F16M 11/14 600/201 |
| 6,273,894 | B1 | 8/2001 | Dykes | |
| 6,491,670 | B1 * | 12/2002 | Toth | A61F 9/007 604/264 |
| 6,706,069 | B2 * | 3/2004 | Berger | A61B 17/8855 623/17.12 |
| 6,730,020 | B2 * | 5/2004 | Peng | A61B 17/02 600/201 |
| 7,476,199 | B2 * | 1/2009 | Spence | A61B 17/02 600/210 |
| 7,717,922 | B2 * | 5/2010 | Neilson | A61F 9/0017 606/107 |
| 7,927,344 | B2 * | 4/2011 | Burba | A61F 9/007 606/107 |
| 8,419,790 | B1 * | 4/2013 | Sabti | A61F 2/1664 606/107 |
| 2004/0225284 | A1 * | 11/2004 | Webb | A61F 9/009 606/5 |
| 2008/0103367 | A1 | 5/2008 | Burba et al. | |

OTHER PUBLICATIONS

International Preliminary Report on Patentability in PCT/US2012/058612 dated Apr. 17, 2014.

* cited by examiner

INTRAOCULAR MANIPULATOR AND RELATED METHODS

CROSS-REFERENCE TO RELATED APPLICATIONS

This application is U.S. national phase filing under 35 U.S.C. §371 of PCT/US12/058612 filed on Oct. 4, 2012, which claims priority from U.S. Provisional Application Ser. No. 61/543,617 filed on Oct. 5, 2011, both of which are incorporated herein by reference.

BACKGROUND

Successfully grasping and manipulating intraocular objects presents considerable difficulties. For example, in connection with cataract surgery, the natural lens of the eye (aka, the crystalline lens) is replaced with an intraocular lens ("IOL"). Cataract prevalence is approximately 20 million, with 2.5 million surgeries per year. Not infrequently, in approximately 2% of cases, IOLs become dislocated (e.g., after a trauma or after a period of time) and must be relocated or replaced. Grasping IOLs presents considerable difficulties. Not only do IOL optics have smooth surfaces making them difficult to grasp, IOL optics are easily damaged (e.g., scratched or torn), rendering conventional forceps less desirable. IOL haptics are even more delicate, and grasping IOLs by their haptic(s) is unwieldy.

As an additional example, in connection with various conditions that render the crystalline lens "loose," e.g., pseudoexfoliation syndrome, it may be necessary to grasp the crystalline lens itself. As above, the crystalline lens is characterized by smooth surfaces making it difficult to grasp and the crystalline lens is itself exceptionally fragile (e.g., capsule may be easily ruptured) and cannot be manipulated with conventional forceps.

By way of further example, foreign bodies sometimes become lodged in the eye and must be retrieved. Given the delicate nature of the retina, extreme care must be taken in grasping such foreign bodies so they do not slip during the retrieval procedure causing, for example, secondary trauma to the retina. Here again, conventional forceps can be inadequate. Other devices in the prior art, including basket forceps and magnets, may also fall short.

What is therefore needed is a device for grasping and manipulating objects intraocularly. The present disclosure addresses this need.

SUMMARY

In accordance with various embodiments, an intraocular manipulator is disclosed which uses negative pressure to grasp and/or manipulate an intraocular object, for example, an IOL, a crystalline lens, or an intraocular foreign body. The device comprises a tip, a stem, and a suction source. Various embodiments may be capable of sustaining a negative pressure at a distal tip opening on an intraocular object having an area of less than about 4.0 mm^2.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

DETAILED DESCRIPTION

Figure 1:
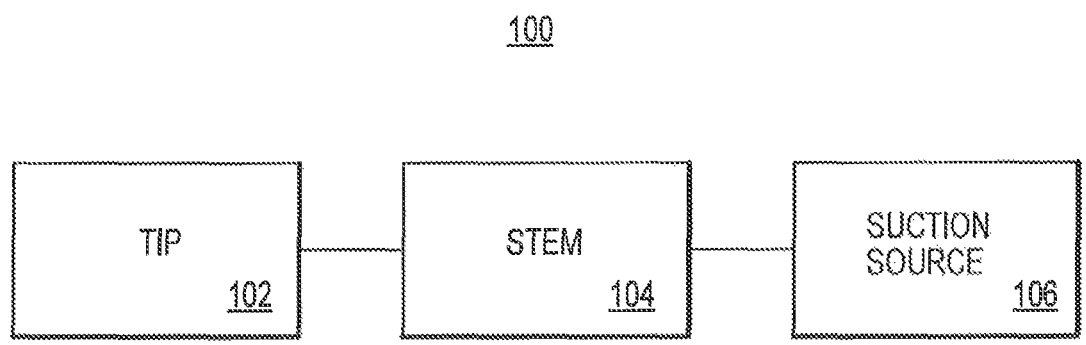
FIG. 1 illustrates a block diagram of an intraocular manipulator.

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

In accordance with various embodiments, an intraocular manipulator is disclosed which uses suction to grasp and/or manipulate an intraocular object, e.g., as an alternative to toothed forceps with their potential for damaging the intraocular object. In accordance with an embodiment, a handheld device is disclosed which uses a suction interface element coupled to aspiration to grasp and/or manipulate an intraocular lens ("IOL") or other intraocular object. In the case of an IOL, a device may be configured to grasp and/or manipulate by the center of the optical portion.

The intraocular manipulator may be particularly useful, inter alia, for cases of dislocated IOLs, phacodonesis, pseudoexfoliation, and intraocular foreign bodies, where conventional forceps are not effective.

With particular reference to FIG. 1, an intraocular manipulator 100, in accordance with an embodiment, comprises a tip 102, a stem 104, and a suction source 106.

Figure 2:
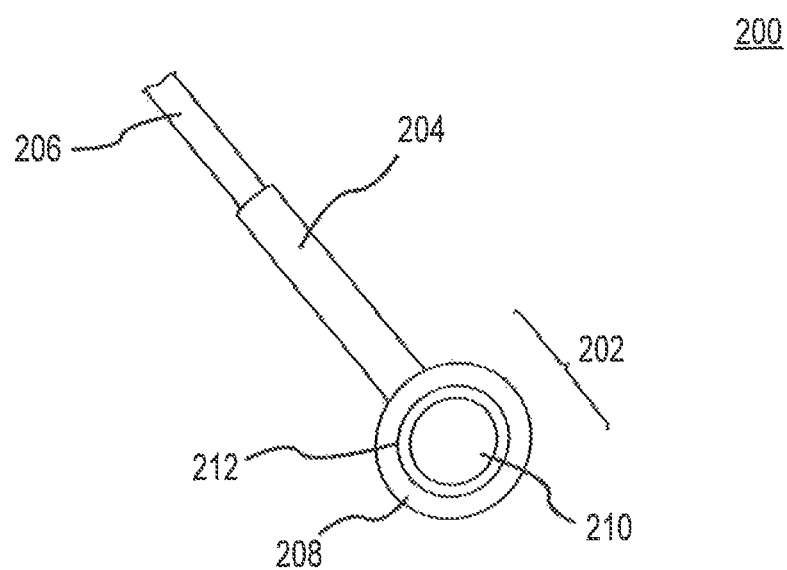
FIG. 2 illustrates a disclosed intraocular manipulator.

Turning now to FIG. 2, in an embodiment, an intraocular manipulator 200 comprises a tip 202, a stem 204, and a suction source 206. Tip 202 may comprise a distal end 208 and a proximal end (not labeled). As used herein, "distal" refers to a portion of an intraocular manipulator 200 nearer to an intraocular object to be grasped and/or manipulated, while "proximal" refers to a portion of an intraocular manipulator 200 further from an intraocular object to be grasped and/or manipulated. The distal end 208 of tip 202 of intraocular manipulator 200, in accordance with an embodiment, is generally configured for contacting an intraocular object. In this regard, and as discussed in more detail below, the distal end 208 of tip 202 may be configured to have a shape and/or size, and/or may be comprised of one or more materials, suitable for grasping and/or manipulating an intraocular object. As used herein, "intraocular object" includes, but is not limited to, an IOL, a crystalline lens, an intraocular foreign body, and various other ocular tissues (e.g., corneal buttons, DSAEK flaps, Descemet's/endothelial flaps, amniotic membrane, etc.).

As it relates to an IOL or the crystalline lens, the distal end 208 of tip 202 may be configured for contacting only the optical portion, without scratching the same. In various embodiments, the distal end 208 of tip 202 may be configured for contacting (i) only the center of the optical portion, (ii) only the anterior surface of the optical portion, (iii) only the posterior surface of the optical portion, (iv) no edge of the optical portion, or (v) no haptic of an IOL.

The distal end 208 of tip 202 may be any shape, for example, circular, oval, triangular, square, polygon shaped or randomly shaped. In an embodiment, the shape of the distal end 208 of tip 202 may be selected (e.g., interchangeable, moldable or adjustable) by a user depending upon the procedure(s) to be performed. In general, the distal end 208 of tip 202 may comprise any shape suitable for grasping and/or manipulating an intraocular object.

Likewise, the distal end 208 of tip 202 may be any suitable size. For example, and in connection with embodiments wherein distal end 208 of tip 202 is circular, it may have an outer diameter of from about 0.5 mm to about 10.0 mm, or more preferably, from about 2.0 mm to about 5.0 mm. More generally, distal end 208 of tip 202 may have a surface area of from about 0.2 mm^2 to about 80.0 mm^2, or more preferably, from about 3.1 mm^2 to about 20.0 mm^2. In an embodiment, the size of the distal end 208 of tip 202 may be selected (e.g., interchangeable, moldable or adjustable) by a user depending upon the procedure(s) to be performed. In an embodiment, the distal end 208 of tip 202 may be dimensioned to contact all or a portion of an intraocular object. In general, the distal end 208 of tip 202 may comprise any size suitable for grasping and/or manipulating an intraocular object.

In various embodiments, the distal end 208 of tip 202 comprises a distal opening 210. Distal opening 210 of tip 202 has a smaller area than the distal end 208 of tip 202, and can be just slightly smaller so as to minimize the crossing profile of intraocular manipulator 200. In this regard, and in connection with embodiments wherein distal opening 210 of tip 202 is circular, it may have an inner diameter of less than about 10.0 mm, or more preferably, less than about 5.0 mm, or most preferably, less than about 2.0 mm. More generally, distal opening 210 of tip 202 may have a surface area of less than about 80.0 mm^2, or more preferably, less than about 20.0 mm^2, or most preferably, less than about 3.1 mm^2.

In various embodiments, the distal end 208 of tip 202 comprises a suction interface element. As used herein, a "suction interface element" is generally any structure configured to provide a conformable interface between an intraocular object and tip 202, and/or to partially or completely maintain suction, aspiration, vacuum, negative pressure or the like (all the foregoing generally referred to as "suction" herein) between an intraocular object and tip 202. In an embodiment, a suction interface element is hemispherically or otherwise concavely shaped (e.g., as with a suction cup), with an aperture at its end through which suction, aspiration, vacuum, negative pressure or the like is transferred.

In more various embodiments, the distal and proximal ends of tip 202 are both open and are in fluid or air communication with one another. Stated differently, tip 202 may comprise a lumen there through.

In various embodiments, the distal end 208 of tip 202 comprises a self-enclosed or self-included mating surface such as a gasket 212. In this manner, gasket 212 may facilitate a waterproof and/or air tight seal between the distal end 208 of tip 202 and an intraocular object. Gasket 212 may further provide for a tip having a smaller diameter without an unwieldy flare.

The distal end 208 of tip 202 generally comprises a flexible material capable of contacting and coupling to an intraocular object, Non-limiting materials include silicones, nitriles, nylons, polycarbonates, polyethylenes, polypropylenes and the like. The flexibility of tip 202 may be such that it conforms to a curved surface (e.g., as with a lens surface) or otherwise irregular surface (e.g., as with the surface of a foreign body). In general, the distal end 208 of tip 202 may comprise any material suitable for grasping and/or manipulating an intraocular object without scratching the same.

In various embodiments, tip 202 further comprises a flexible material or a structural support member configured to add support to tip 202, for instance, for coupling to stem 204.

Thus, in various embodiments, the proximal end of tip 202 is configured to couple to stem 204, which is a generally longitudinally extending structure with a lumen there through (e.g., a cannula, tube, catheter, rod or the like). Stem 204 can provide structural support to intraocular manipulator 200. The coupling between the proximal end of tip 202 and stem 204 may be temporary or permanent and may be rotatable.

Figure 3A:
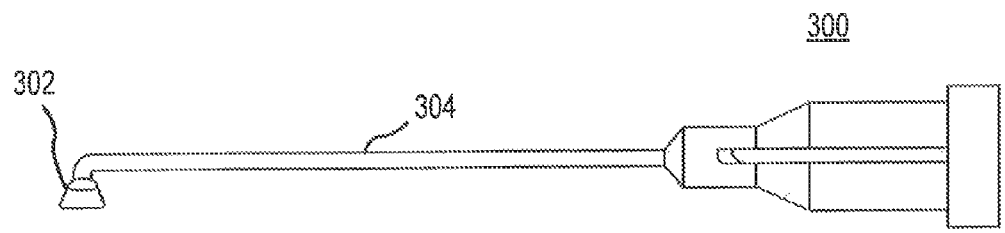
FIGS. 3A and 3B illustrate an intraocular manipulator having a rotatable tip.
Figure 3B:
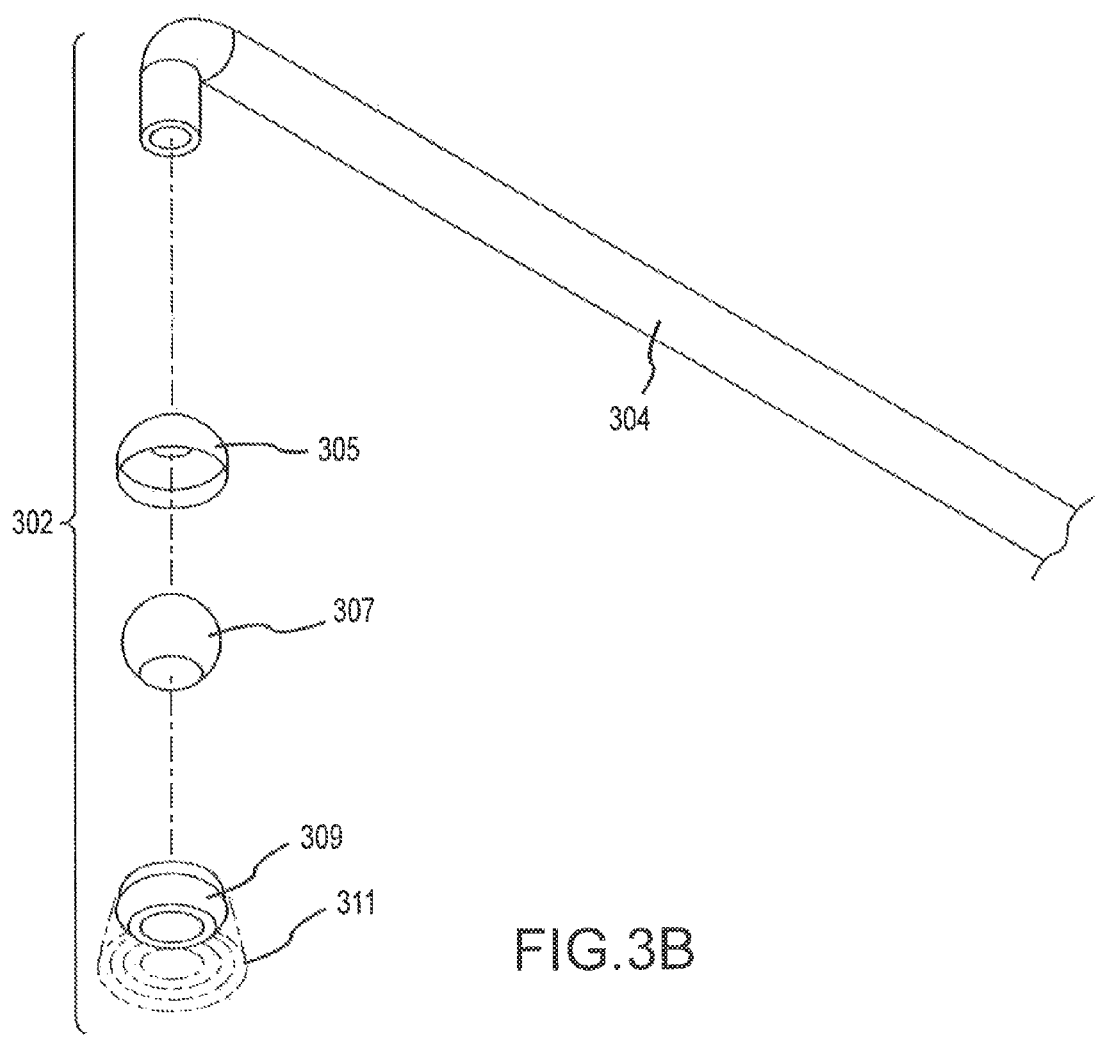

For example, and with momentary reference to FIGS. 3A and 3B, an intraocular manipulator 300 can comprise a stem 304 that is coupled to a tip 302. In an embodiment, tip 302 is rotatable. Various configurations within the scope of the present disclosure can accomplish this functionality, as long as a pathway for suction is maintained. In the embodiment illustrated in FIG. 3B, rotation of tip 302 is accomplished by the inclusion of a bearing 305 coupled to stem 304, a ball 307, and a cap 309 covering ball 307 and rotatably coupled to bearing 305. Cap 309 can comprise the distal end of tip 302, or a further structure, for example a flexible material 311 capable of contacting and coupling to an intraocular object, can comprise the distal end of tip 302.

In an embodiment, stem 204 may comprise a distal end and a proximal end. Structurally, the proximal end of tip 202 is configured to couple to the distal end of stem 204, and the proximal end of stem 204 is configured to couple to suction source 206.

In various embodiments, the distal portion of stem 204 is angled with respect to distal opening 210 at the distal end 208 of tip 202. For instance, the distal portion of stem 204 may be substantially perpendicular to distal opening 210 at the distal end 208 of tip 202. In other various embodiments, the primary axis of stem 204 is angled with respect to distal opening 210 at the distal end 208 of tip 202. In yet other various embodiments, the primary axis of stem 204 is angled with respect to the direction suction is applied at the distal end 208 of tip 202. In still other various embodiments, the direction stem 204 crosses ocular tissue is angled with respect to the direction suction is applied at the distal end 208 of tip 202.

Adjusting the angle in this manner may facilitate access of intraocular manipulator 200 through the cornea. For example, stem 204 may be at a steeper angle or no angle at all when designed for grasping a foreign body. Alternatively, and with momentary reference to FIG. 4, stem 404 of intraocular manipulator 400 may be substantially at a right angle to an opening 410 at the distal end 408 of tip 402 when grasping an IOL or crystalline lens. As an aside, and as described above, a gasket 412 may be incorporated to, inter alia, facilitate a waterproof and/or air tight seal.

Figure 4:
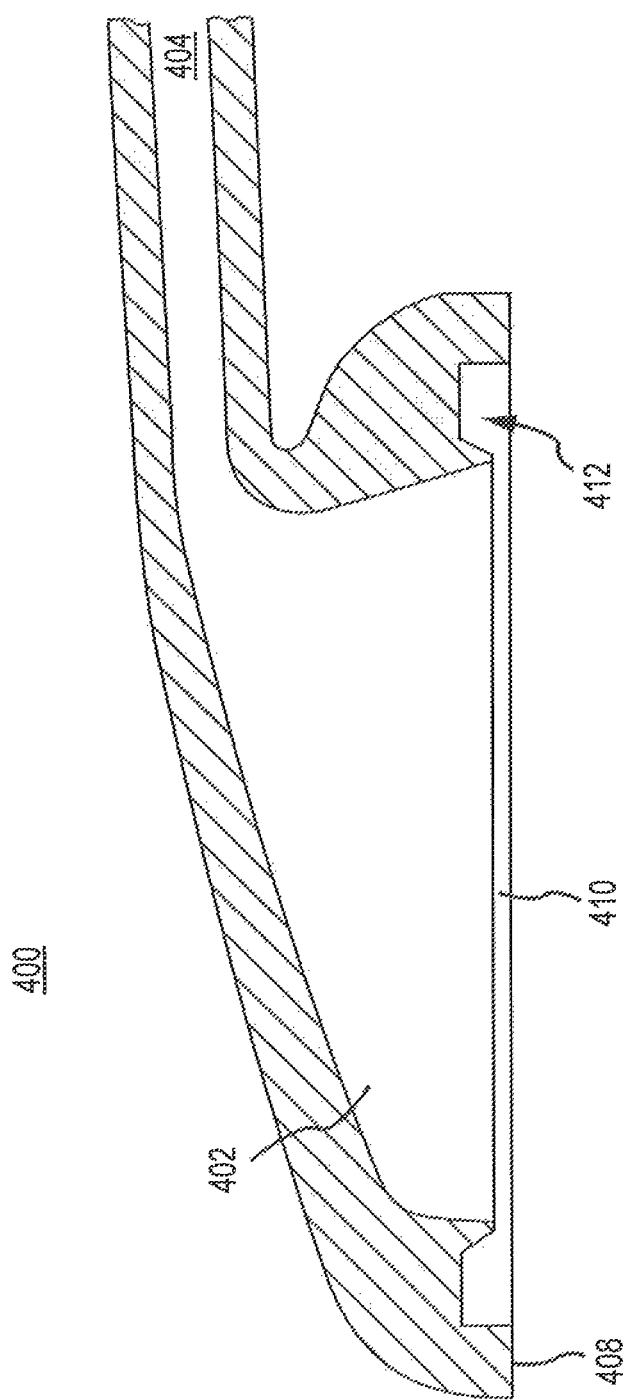
FIG. 4 illustrates a cross-sectional view of an intraocular manipulator.

In various embodiments, the coupling between stem 204 and tip 202 is angularly adjustable. Angular adjustability may be accomplished, inter alia, by incorporating a flexible material, a material having a weakened portion, one or more folded elements, one or more hinged elements, and the like. In various embodiments, stem 204 and tip 202 are integral with one another, for example manufactured from a single mold or extrusion, as illustrated in FIG. 4.

To further minimize the crossing profile of intraocular manipulator 200, tip 202 may be collapsible, for example, collapsible and retractable within stem 204. For example, tip 202 can comprise foldable or otherwise collapsible edges, so that tip 202 can be inserted and/or removed through a small gauge surgical opening, wound, trocar, or port (e.g., less than 20, 23, or 25 gauge). In various embodiments, edges of tip 202 can then be expanded or otherwise deployed from the folded or otherwise collapsed configuration once in the eye. Various configurations within the scope of the present disclosure can accomplish this functionality. In one embodiment, tip 202 is folded or otherwise collapsed into a surrounding cartridge, and then pushed through the surgical opening, wound, trocar, or port, during or after which the surrounding cartridge is removed.

Stem 204 may comprise a rigid material, such as plastics, metals, alloys and the like, or a flexible material, such as silicones, nitriles, nylons, polycarbonates, polyethylenes, polypropylenes and the like. Importantly, the material from the distal end to the proximal end of stem 204 may vary. For instance, it may be desirable to have a more rigid material at the distal and/or proximal end of stem 204 for coupling to tip 202 and/or suction source 206, while it may be desirable to have a more flexible material between the distal and proximal ends of stem 204.

In various embodiments, the proximal end of stem 204 is configured to couple to suction source 206. The coupling may be temporary or permanent. Suction source 206 is generally any device configured to supply suction, aspiration, vacuum, negative pressure or the like. In accordance with various embodiments, suction source 206 comprises a syringe, an aspirator, a pump or a machine, for example, having suction controlled by actuating a foot pedal. Stem 204 and suction source 206 may together comprise a vitrectomy cutter or another intraocular luminal instrument, such as those currently known in the art.

By way of non-limiting example, a suction interface element of the device may be placed over the tip of a vitrectomy probe, so that concurrent vitrectomy may be performed while removing an intraocular object from the vitreous cavity of the eye.

Suction source 206 may comprise fluid (e.g., saline or water) or air suction. The seal made by suction source 206 at an opening at the distal end of tip 202 may be released, for example, by opening a valve, letting air back in via a syringe, or disengaging a foot pedal.

In accordance with an embodiment, suction source 206 is configured to generate enough suction to sustain a negative pressure at a distal tip opening of at least 10 milliNewtons without breaking suction, more preferably at least 30 mN, at least 40 mN, at least 150 mN, at least 250 mN, or more. Notwithstanding the foregoing, and in general, the pressure may be suitably selected and/or adjusted to be stronger or more delicate depending on what intraocular object is being grasped and/or manipulated. For instance, the pressure to grasp a crystalline lens may be less than the pressure to grasp an intraocular foreign body, to which damage is not a concern.

Various embodiments of suction source 206 may be capable of sustaining such negative pressure at a distal tip opening on an intraocular object having an area of less than about 80.0 mm^2, more preferably less than about 20.0 mm^2, most preferably less than about 3.1 mm^2.

In various embodiments, the device is configured to be handheld. In various embodiments, the device is configured to be a standalone device, while in other various embodiments, the device is configured to be an accessory to an existing device. In addition, the device may be used in conjunction with other intraocular devices.

Figure 5:
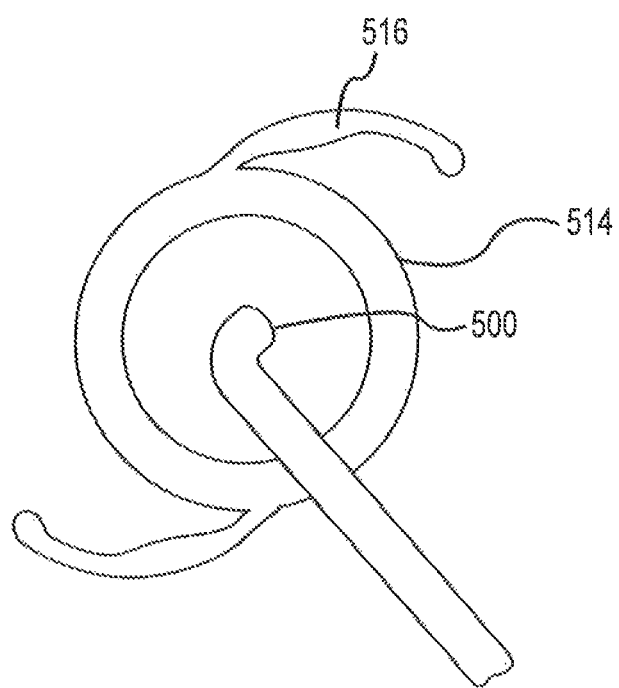
FIG. 5 illustrates an intraocular manipulator grasping an IOL.

Various embodiments further comprise methods relating to the intraocular manipulators described herein. As noted previously, the intraocular manipulator may be useful in connection with a wide variety of procedures where conventional forceps are not effective, inter alia, for cases of dislocated IOLs, phacodonesis, pseudoexfoliation, and intraocular foreign bodies. In one such procedure, and with reference to FIG. 5, an intraocular manipulator 500 may be used to grasp and/or manipulate an IOL 514 without scratching IOL 514 and without contacting a haptic 516 of IOL 514.

A method comprises the steps of: (i) gaining surgical access if needed to an intraocular object, (ii) contacting the intraocular object with a distal opening of an intraocular manipulator, (iii) applying suction to the distal opening through the intraocular manipulator, (iv) grasping and/or manipulating the intraocular object according to the intended procedure, and (v) releasing the seal made at the distal opening.

Optional additional steps may comprise: (i) clamping the stem to maintain suction at a distal opening of an intraocular manipulator, and (ii) performing a secondary procedure, for example, securing an IOL or the crystalline lens, closing a tissue opening, performing a suturing step, or any other intraocular procedure. During the secondary procedure, the ability to maintain suction at a distal opening of an intraocular manipulator may offer significant advantages over the prior art in terms of both grasping and manipulating intraocular objects.

A method may further comprise applying a liquid or gel to one or both of the intraocular objects and a portion of the intraocular manipulator, prior to the step of contacting the intraocular object to enhance the step of grasping and/or manipulating the intraocular object.

In yet another embodiment, contrast or some therapeutic agent may be injected through the stem (e.g., Kenalog® to stain the vitreous of the eye or a medicant as dictated by the particular procedure).

Various embodiments have been subjected to surgical testing. A freshly enucleated porcine eye was used in one test. In that test, first, a keratome was used to make a 2.4 mm wound in the cornea, through which a scleral depressor was used to disinsert the zonules from the lens, allowing the crystalline lens to be extruded through a pars plana incision. A 2 mm silicone intraocular manipulator was then used to grasp the crystalline lens outside the eye.

Next, the lens was disinserted but kept within the eye. A 2 mm silicone intraocular manipulator was then used to grasp the dislocated crystalline lens and bring it forward. The results demonstrate disclosed intraocular manipulators would be particularly useful in cases of pseudoexfoliation and trauma, where the lens may be partially dislocated already, but accessible anteriorly. Disclosed intraocular manipulators could also be used to hold the lens while performing phacoemulsification or other intraocular procedures such as in situ phacofragmentation or vitrectomy.

Next, the crystalline lens was removed. An IOL was placed in sulcus, badly dislocated with the haptics oriented vertical. The results demonstrate the ability of disclosed intraocular manipulators to get control of the lens and bring it forward to be sutured to the iris.

Finally, a porcine eye was prepared with the anterior segment removed, gel removed, and a metallic intraocular body placed over retina. An intraocular manipulator was able to grasp the intraocular body and remove it safely, despite evolving retinal detachment.

Figure 6:
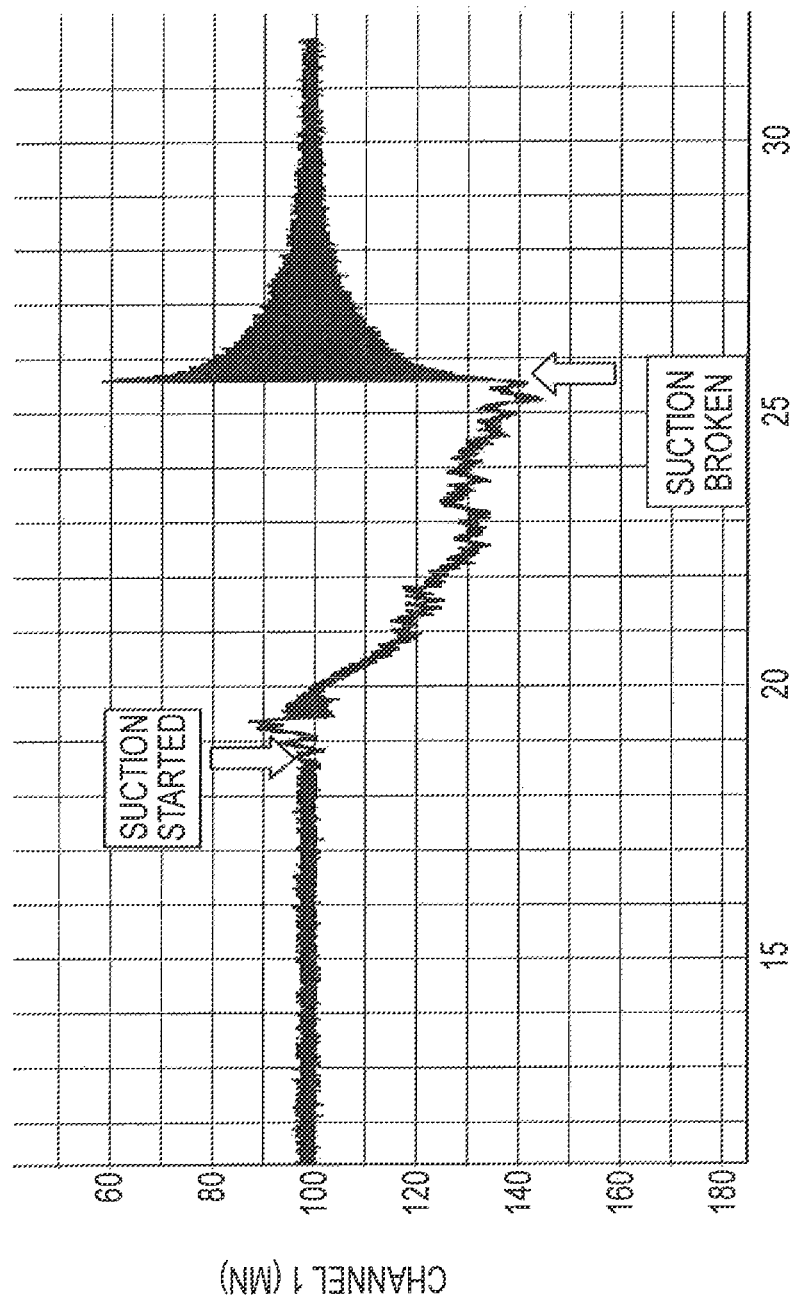
FIG. 6 illustrates a typical force recording profile for an intraocular manipulator.

Various embodiments were also subjected to laboratory testing. Tested was comparative suction force of 6 different intraocular manipulators of different materials and sizes. Each intraocular manipulator was placed on a spring-loaded, syringe-driven tubing system filled with water to create suction. An IOL submerged in water was grasped with the intraocular manipulator, and an ADI force transducer system was used to record results. FIG. 6 illustrates a typical force recording profile for an intraocular manipulator and the numbers shown in Table 1 below reflect the force at which suction was broken for various disclosed intraocular manipulators.

TABLE 1

|  | Trial | | | | | |
| --- | --- | --- | --- | --- | --- | --- |
|  | 1 | 2 | 3 | 4 | 5 | 6 |
|  | Material | | | | | |
|  | Nitrile | Silicone | Diff Silicone | Silicone | Nitrile | Silicone |
| Width (mm) | 3.5 | 2 | 2 | 5 | 5 | 4 |
| F (mN) | 36.0379 | 17.6512 | 16.9158 | 41.1862 | 18.3867 | 34.567 |
| F (mN) | 36.7734 | 7.3547 | 11.032 | 38.9798 | 44.8635 |  |
| F (mN) | 44.8635 |  | 6.6192 | 28.6832 | 30.8896 |  |
| Average F (mN) | 39.22493 | 12.5 | 11.5 | 36.3 | 31.4 | 34.6 |

The iterations of the intraocular manipulator tested showed flexibility and resistance to loss of grasp from the intraocular forces that could be expected to be encountered during various intraocular maneuvers. Additional testing of the intraocular manipulator demonstrated its ability to re-grasp and continue to stabilize an intraocular object when displacement forces were excessive. Still more testing demonstrated the intraocular object position on the intraocular manipulator could be gently adjusted without loss of grasp.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

By way of example, the present disclosure should not be construed as limited to grasping intraocular objects, but grasping objects in other settings as well, whether surgical or non-surgical.

We claim:

1. A device for grasping an intraocular object comprising:
a tip having a proximal end and a distal opening, wherein said distal opening has a surface area of less than about 20.0 mm^2;
a suction source configured to apply negative pressure without breaking a seal at said distal opening, and
a stem comprising a flexible material and having a lumen extending there through configured to couple said proximal end with said suction source, wherein said stem is rotatably coupled to said tip in an assembled configuration,
wherein the tip is configured to rotate about the stem along an axis of rotation and wherein the axis of rotation and the distal opening are concentric and perpendicular.

2. A device for grasping as in claim 1, wherein said tip comprises a suction interface element.

3. A device for grasping as in claim 2, wherein said tip comprises a gasket.

4. A device for grasping as in claim 3, wherein said tip is comprised of a material selected from a group consisting of silicones and nitriles.

5. A device for grasping as claim 4, wherein said tip is conformable to a curved or otherwise irregular surface.

6. A device for grasping as in claim 1, wherein said distal opening has a diameter of less than about 5.0 mm.

7. A device for grasping as in claim 1, wherein said stem is angled with reference to said distal opening.

8. A device for grasping as in claim 7, wherein said stem is angularly coupled to said suction source.

9. A device for grasping as in claim 8, wherein said stem is rotatably coupled to said tip by a rotatable coupling between said tip and said stem, the rotatable coupling comprising a ball and a bearing.

10. A device for grasping an intraocular object comprising:
a tip having a proximal end and a distal opening, wherein said distal opening has a surface area of less than about 20.0 mm^2;
a suction source configured to apply negative pressure without breaking a seal at said distal opening, and
a stem comprising a flexible material and having a lumen extending there through configured to couple said proximal end with said suction source, wherein said stem is rotatably coupled to said tip in an assembled configuration,
wherein the tip is configured to rotate about a distal end of the stem along an axis of rotation and wherein the distal opening is rotationally symmetric about the axis of rotation.

11. A device for grasping as in claim 10, wherein said stem is angled with reference to the axis of rotation.

12. A device for grasping as in claim 10, wherein said stem is parallel with reference to the axis of rotation.

13. A device for grasping as in claim 10, wherein said stem is rotatably coupled to said tip by a rotatable coupling between said tip and said stem, the rotatable coupling comprising a ball and a bearing.

14. A device for grasping an intraocular object comprising:
a tip having a proximal end and a distal opening;
a suction source configured to apply negative pressure without breaking a seal at said distal opening, and
a stem comprising a flexible material and having a lumen extending there through configured to couple said proximal end with said suction source, wherein said stem is rotatably coupled to said tip in an assembled configuration,
wherein the tip is configured to rotate about an axis of rotation of the stem and wherein the distal opening is rotationally symmetric about the axis of rotation of the stem.

15. A device for grasping as in claim 14, wherein said stem is rotatably coupled to said tip by a rotatable coupling between said tip and said stem, the rotatable coupling comprising a ball and a bearing.

* * * * *